United States Patent [19]
Hodgen et al.

[11] Patent Number: 5,116,818
[45] Date of Patent: May 26, 1992

[54] METHOD AND KIT FOR CONTRACEPTION WITH GNRH-ANTAGONIST

[75] Inventors: Gary D. Hodgen, Norfolk, Va.; Daniel Kenigsberg, Stony Brook, N.Y.

[73] Assignee: Medical College of Hampton Roads, Norfolk, Va.

[21] Appl. No.: 565,029

[22] Filed: Aug. 9, 1990

Related U.S. Application Data

[63] Continuation-in-part of Ser. No. 24,205, Mar. 10, 1987, abandoned.

[51] Int. Cl.$^5$ ............................................. A61K 37/38
[52] U.S. Cl. ......................................... 514/15; 514/2; 530/313; 530/328; 930/110; 930/DIG. 801; 930/DIG. 802; 930/DIG. 690; 930/DIG. 800
[58] Field of Search ...................... 530/313, 328, 398; 514/2, 15, 800, 178; 930/110, DIG. 690, DIG. 800, DIG. 802, DIG. 801

[56] References Cited

U.S. PATENT DOCUMENTS

| | | | |
|---|---|---|---|
| 4,143,136 | 3/1979 | De Jage et al. | 514/178 |
| 4,481,190 | 11/1984 | Nestor et al. | 530/328 |
| 4,762,717 | 8/1988 | Crowley et al. | 514/800 |

FOREIGN PATENT DOCUMENTS 2253916  9/1973  Fed. Rep. of Germany ...... 514/178

OTHER PUBLICATIONS

Santoro et al., Endocrine Reviews, vol. 7, No. 1, pp. 11–23 (1986).
Kenigsberg et al., Endocrine Reviews, vol. 7, No. 1 pp. 34–43, 1986.
Danforth et al., "Intermittent GnRH Antagonist Plus Progestin Contraception Conserving Tonic Ovarian Estrogen Secretion and Reducing Progestin Exposure", Contraception, Jun. 1990, vol. 41, No. 6, pp. 623–631.
Williams, R. F., and Hodgen, G. D., "The Reproductive Cycle in Female Macaques", American Journal of Primatology Supplement, 1:181–192 (1982).
Goodman, A. L., and Hodgen, G. D., "The Ovarian Triad of the Primate Menstrual Cycle", Recent Progress in Hormone Research, vol. 39:1–73.
Dizerega, G. S. and Hodgen, G. D., "Folliculogenesis in the Primate Ovarian Cycle", Endocrine Reviews, vol. 2, No. 1:27–49.
Henderson et al., "Re-evaluating the role of progestogen therapy after the menopause", Fertility and Sterility, vol. 49 (Suppl.), No. 5 May 1988.
GnRH Analog Design, Karten et al., vol. 7, No. 1, Feb. 1986 pp. 44–66.
GnRH Antagonist Inhibits Ovulation, Kenigsberg et al., JCE & M 1986, vol. 62, No. 4, pp. 734–738.
J. Clin. Endocrinol. Metab. 56(4), 844–8, CA 99(3), 16882u, Werlin et al. (1983).
Gregory Pincus, Control of Fertility in Mammals by Hormonal Steroids, vol. 157, pp. 53–62.

Primary Examiner—Lester L. Lee
Assistant Examiner—T. D. Wessendorf
Attorney, Agent, or Firm—Millen, White & Zelano

[57] ABSTRACT

A method of providing contraception for and regulation of the menstrual cycle of a gonadal female mammal by a) administering thereto about once a week throughout her menstrual cycle an amount of a GnRH-antagonist effective to block folliculogenesis and thereby achieve a contraceptive state but less than the amount thereof required to block hormonogenesis; and b) inducing menses by administering during the last half of that cycle an amount of a progestin effective to produce a secretory endometrium and then terminating the progestin administration.

15 Claims, No Drawings

METHOD AND KIT FOR CONTRACEPTION WITH GNRH-ANTAGONIST

This is a continuation-in-part of application Ser. No. 07/024,205, filed Mar. 10, 1987, now abandoned.

BACKGROUND OF THE INVENTION

This invention relates to a method and kit for achieving contraception in gonadal female mammals with GnRH-antagonists without inducing an agonadal state.

Although inhibition of ovulation in the form of estrogen/progestin combination oral contraceptives has been the most effective strategy for achieving reversible pharmacological fertility control in women, because of the known adverse side-effects associated with long term contraception by this method, especially in women who smoke in the 40-44 age group, there is increasing interest in contraception achieved through GnRH analogs that act on the pituitary to induce a hypogonadotropic status. GnRH-agonists do so after a transient stimulatory phase that lasts from 1-3 weeks. Monroe, S. E. et al. Fertil Steril 1985; 43:361; Berquist, C. et al., Contraception, 1979, 19:497. In contrast, GnRH-antagonists lack stimulatory activity, causing prompt reduction of gonadotropin secretion and an agonadal state Kenigsberg, D. et al., Dose-response using a gonadotropin-releasing hormone antagonist. Fertil Steril, 1984, 42:116; Kenigsberg, D. et al., Fertil Steril 1984, 42:116.

As reported by us in J. Clin. Endocrinol. Metab. 62: 734 (April, 1986), the contents of which article are incorporated herein by reference, we have now found that reliably effective contraception (by inhibition of ovulation) can be achieved with GnRH-antagonists in gonadal female mammals without blocking hormonogenesis, thereby avoiding the side effects associated with a long term agonadal state.

For more than a decade, reproductive endocrinologists have sought an adequate strategy to employ GnRH analogs (agonists and antagonists) for contraception in women. Almost uniformly, enthusiasm to move ahead has been thwarted by the knowledge that a persistent functional hypopituitary status, induced by GnRH analogs, is associated with relative ovarian quiescence and a hypoestrogenic milieu. In turn, the expected consequences include hot flushes, urogenital tissue atrophy and bone mineral loss (osteoporosis). Among women of reproductive age this would surely require steroidal replacement therapy (estrogen and progestin), mimicking familiar treatment regiments in postmenopausal women. Indeed, there seems to be little gain in a method based on such complex pharmacology, where the potential consequences of side effects may exceed those of the common oral contraceptives containing similar or the same synthetic steroids. Also, there have been questions about the long-term tolerance to and safety of the GnRH analogs themselves at dosages which achieve an agonadal state.

In accordance with this invention, it is now possible to employ GnRH-antagonists for reliable ovulation inhibition, while avoiding frank estrogen deficiency and relying on natural ovarian steroids to maintain normal metabolic homeostasis.

OBJECTS OF THE INVENTION

It is an object of this invention to provide a method for achieving contraception in a gonadal female mammal with a GnRH-antagonist without blocking hormonogenesis.

Another object is to provide such a method which does not interfere with menses, and which regulates the onset thereof.

Still another object is to provide such a method in which the medication is self-administered.

A further object is to provide such a method which does not have the side effects associated with estrogen-progestin oral contraception.

Another object is to provide kits for practicing the method of this invention.

Other objects will be apparent to those skilled in the art to which this invention pertains.

SUMMARY OF THE INVENTION

In a method aspect, this invention relates to a method of contraception and regulation of the menstrual cycle of a gonadal female mammal, which comprises a) administering thereto at about weekly intervals throughout her menstrual cycle, beginning on day 1, 2 or 3 menses, an amount of a GnRH-antagonist effective to block folliculogenesis, thereby creating a contraceptive state during that cycle, but less than the amount thereof required to block hormonogenesis, and b) inducing menses by administering thereto during about the last two weeks of that cycle an amount of a progestin effective to produce a secretory endometrium and then terminating the progestin administration.

In a kit aspect, this invention comprises a kit in the form of a dispenser-type package containing (a) sufficient dosage units of a GnRH-antagonist, in a dosage form suitable for self-administration, to block gametogenesis but not hormonogenesis in a gonadal female mammal for about one calendar month; (b) sufficient dosage units of a progestin, also in a dosage form suitable for self-administration only during the last 1 to 2 weeks of each cycle prior to menses to produce a secretory endometrium in the female mammal and to induce menses after administration of the progestin is terminated; and, optionally, (c) sufficient dosage units of a placebo of the same dosage form as that of the GnRH-antagonist and/or of the progestin to permit the administration daily of a single dosage unit containing inappropriate sequence, the GnRH-antagonist and/or the progestin or a placebo throughout the menstrual cycle or for about the first 20-25 days of the menstrual cycle prior to onset of menses.

DETAILED DISCLOSURE

The about weekly, viz., about every 5-9 days, administration of the GnRH-antagonist achieves fertility control in gonadal female mammals, e.g., husbandry animals and humans, by acutely suppressing the release of endogenous luteinizing hormone and follicle stimulating hormone from the pituitary gland, thereby preventing maturation of the dominant follicle and release of oocytes. However, the about weekly administration of the GnRH-antagonist does not impair adequate ovarian estradiol secretion. To distinguish the regulation of the two ovarian activities, viz., as an organ of reproduction and a gland of internal secretion, the term "folliculogenesis" is used herein to refer to the gametogenic activity and "hormonogenesis" refers to the secretory activity. It is known that hypoestrogenic states can cause hot flashes, increase the risk of osteoporosis, and precipitate urogenital atrophy in women. The intermittent, i.e., about weekly, use of the GnRH-antagonist for fertility control according to this invention avoids these symptoms by maintaining a near normal follicular phase level of serum estradiol by distinguishing blockage of hormonogenesis (which is sustained) from gametogenesis (which is inhibited).

In the normal menstrual cycle, progesterone is produced from the corpus luteum created after ovulation. Since ovulation is prevented, in the contraceptive method employed in this invention progesterone secretion remains low. Therefore, a progestin is also administered, but only toward the end of each regulated cycle, in order to convert proliferative endometrium to the secretory phase, thereby reducing the risks of endometrial carcinomas associated with unopposed estrogen action. Because the progestin is administered only during about the last two weeks of each cycle and because contraception is achieved with the GnRH-antagonist alone the progestin is not required nor is it employed in order to achieve a reliable contraceptive state.

Examples of progestins which can be employed in this invention are micronized progesterone (50-150 mg/day), norethindrone (0.5-2.5 mg/day), norethynodrel (1 mg/day); ethynodiol diacetate (1-2 mg/day), norgestrel (0.2-0.5 mg) and levo-norgestrel (0.1-0.3 mg/day).

The progestin can be administered in the conventional manner by any route that the selected progestin is active. Most synthetic progestins are orally active and therefore are preferably administered by that route, e.g., in the form of a tablet, dragee, capsule or pill. If the progestational agent of this invention is to be administered in tablet or dragee form, it may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected. The progestin can also be administered intranasally, as a suspension or dispersion in an appropriate vehicle, by inhalation as an aerosol discharged from a conventional inhalator, sublingually, in the form of a lozenge, rectally or intravaginally, e.g., in the form of a suppository, alone or in admixture with the GnRH-antagonist, when appropriate according to the day of the menstrual cycle when administered. Other means are by an implant which discharges the progestin, for about 7-15 days, about 14-16 days after implant, (e.g., beginning about two weeks prior to the desired date of onset of menses); intradermally, as a skin patch containing a mixture of the progestin and a skin penetrant, e.g., DMSO; or imbedded in a vaginal ring which discharges the progestin for the desired number of days after insertion.

An example of a GnRH-antagonist which can be employed in this invention is [Ac-D4ClDPhe$^1$, D4ClDPhe$^2$, DTrp$^3$, DArg$^6$, DAla$^{10}$)GnRH. Others are known in the prior art. See, e.g., 4,409,208; 4,547,370; 4,565,804; 4,569,927; and the 4,619,914, whose disclosures are incorporated herein by reference. Such other antagonists include:

[Ac-4ClDPhe$^2$, D3Pal$^3$, Arg$^5$, D$_2$Nal$^6$, DAla$^{10}$]GnRH
[Ac-D$_2$Nal$^1$, 4ClDPhe$^2$, DTrp$^3$, DArg$^6$, DAla$^{10}$]GnRH
[Ac-D$_2$Nal$^1$, 4FDPhe$^2$, DTrp$^3$, DArg$^6$]GnRH
[Ac-D$_2$Nal$^1$, 4ClDPhe$^2$, DTrp$^3$, DhArg(Et$_2$)-$^6$DAla$^{10}$]GnRH
[Ac-Nal$^1$, DME4ClPhe$^2$, DPal$^3$, Ser$^4$, Tyr$^5$, DArg$^6$, Leu$^7$, ILys$^8$, Pro$^9$, DAla$^{10}$]GnRH.

After the first dose of a GnRH-antagonist is administered, a gametogenesis blocked state, i.e., a contraceptive state, is usually achieved within about 7 days thereafter, provided the first dose of the GnRH-antagonist is administered on day 1, 2 or 3 of menses. Administration after day 3 may not abate selection of the oncoming dominant-follicle during that menstrual cycle and therefore another form of contraception should be practiced during that cycle, or at least during the potentially fertile days thereof.

The GnRH-antagonists employed in this invention can be administered in the form of pharmaceutically acceptable, nontoxic salts, such as acid addition salts, or of metal complexes, e.g., with zinc, barium, calcium, magnesium, aluminum or the like, or of combinations thereof. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like.

The pharmaceutical compositions employed in the process of this invention will usually contain the GnRH-antagonist in conjunction with a conventional, pharmaceutically acceptable carrier. Usually, the effective dosage of the GnRH-antagonist is from about 1 to about 100 micrograms of the GnRH-antagonist per kilogram of the body weight of the host when given intravenously; therefore, oral dosages and dosages by other routes will be higher. Overall, treatment of subjects with these GnRH-antagonists is generally carried out in the same manner as other clinical treatments using GnRH-antagonists, except for the total amount thereof which is administered.

The GnRH-antagonists can be administered to the mammal intravenously, subcutaneously, intramuscularly, sublingually, orally by inhalation, percutaneously, rectally, intranasally or intravaginally, to achieve contraception. Effective dosages will vary with the selected mode of administration and the particular species of mammal being treated. An example of one typical dosage form is a bacteriostatic water solution containing the GnRH-antagonist which solution is administered as a nasal mist to provide a dose in the range of about 0.1 to 2.5 mg/kg of body weight. Oral administration of the GnRH-antagonist may be in the form of a lozenge, to be dissolved under the tongue, or as an aerosol, to be inhaled.

Optionally, one or two of the doses of GnRH-antagonist can be administered in admixture with doses of the progestin on appropriate days of the cycle, e.g., day 15 or 16 and day 22 or 23.

In its article of manufacture embodiment, this invention relates to materials, reagents and kits for practicing the method of this invention.

In one form of its kit aspect, this invention is directed to a two-stage multiple dosage unit article of manufacture comprising a) four dosage units, adapted for self-administration, each dosage unit containing an amount of a GnRH-antagonist effective when one unit thereof is administered every seven days, the first on day 1, 2 or 3 of menses, to block folliculogenesis for one cycle but which is less than the amount thereof effective to block hormonogenesis; and b) 5-12 units, adapted for self-administration, during the last two weeks of the menstrual cycle, collectively containing an amount of a progestin effective, when a dosage unit is administered daily on successive days, beginning e.g., on day 14, 15 or 16 of the cycle until all of the units have been administered, to produce a secretory endometrium and thereafter induce menses when its administration is terminated. Optionally, the kit also comprises a plurality of placebo dosage units corresponding to those of a) which collectively therewith total about 23 to about 28 units, the GnRH-antagonist-containing, the progestin-containing and the placebo units being arranged in appropriate sequential order. Optionally also, the third and fourth GnRH-antagonist-containing dosage unit is contained in the same dosage units which contain the progestin. Preferably, the GnRH-antagonist units are adapted for sub-lingual, rectal, vaginal or topical (on the skin) application. Preferably also, the progestin units are adapted for oral ingestion e.g., tablets, capsules or dragees, or for administration by the same route as the GnRH-antagonist units. Preferably further, the GnRH-antagonist units, the progestin dosage units and any placebo dosage units all are adapted for administration by the same route.

In another form of its kit aspect, this invention is directed to a combination of (a) a nasal spray plastic squeeze bottle containing a GnRH-antagonist in a vehicle adapted for administration thereof as a mist, at a concentration effective upon squeezing the bottle either once, twice or three times while the dispensing tip is inserted into a nostril of the female mammal, once every seven days, an amount of the antagonist effective to block folliculogenesis and thereby achieve a contraceptive state but less than the amount required to block hormonogenesis; and 5–12 individual dosage units, preferably adapted for oral ingestion, e.g., tablets or capsules, collectively containing an amount of a progestin effective upon administration thereof during the last half of the menstrual cycle to produce a secretory endometrium and to thereafter induce menses, or 23 or 28 such individual dosage units arranged in appropriate sequential order, 5 to 11 of which units e.g., Nos. 15 to 19–26, contain the progestin and the remainder are placebos, to be taken daily for the first 23 days of a menstrual cycle or every day of a 28 day menstrual cycle.

In a further kit form, instead of the nasal spray squeeze bottle a plurality of skin patches or an aerosol inhaler is employed to dispense the required amount of GnRH-antagonist.

In still another kit form, both the GnRH and progestin are in a unit dosage form adapted for vaginal or rectal administration, e.g., suppositories. For example, such a kit comprises 4 suppositories containing the GnRH-antagonist and either 5–8 separately identified suppositories containing the progestin for administration on successive days of the third week of one menstrual cycle, or the kit comprises 23 to 28 such suppositories, arranged for sequential administration, every 7th one of which contains the GnRH-antagonist; the 16th through the 22nd of which contain the progestin; and the remainder are placebos.

In alternative embodiments, the test kit contains the GnRH-antagonist incorporated in another delivery system, e.g., adhesive skin patches containing the medication in an intradermal and delivery system for application to the skin; suppositories for administration of the medication rectally or vaginally; an inhaler for delivery of the medication as an aerosol, or lozenges for administration sublingually; in each case once or twice daily on the same or on two successive days of each week.

The materials, reagents and kits optionally and preferably also contains instructions for administering the GnRH-antagonist and the progestin.

A specific example of materials, reagents and kits of this invention intended for use by a gonadal female who is to be rendered infertile but not agonadal is a box with lid containing (a) a conventional nasal mist squeeze bottle containing a GnRH-antagonist, in an inert, physiologically acceptable carrier in which the antagonist is stable, at a concentration effective to deliver into the nostril, when the bottle is squeezed twice while the dispensing tip thereof is inserted into the nostril, an amount of the GnRH-antagonist effective to place the female in a folliculogenesis blocked state for 7 days, and containing an amount thereof sufficient for four such administrations on a weekly basis throughout one menstrual cycle, and (b) seven to 11 tablets of an orally active progestin effective when taken orally on successive days, e.g., beginning on day 15 of the menstrual cycle, to produce a secretory endometrium and thereafter to induce menses. If eleven progestin tablets are employed, about a 30-day cycle will usually be achieved whereas a lesser number will produce a correspondingly shorter cycle.

About weekly GnRH-antagonist therapy alone according to this invention blocks folliculogenesis while sustaining hormonogenesis. The maintenance of hormonogenesis provides circulating estrogen levels sufficient to preclude hypoestrogenic effects. The blockage of folliculogenesis prevents the selection and maturation of a functional dominant follicle. Consequently, anovulation ensues concurrently with subnormal levels of luteal phase serum progesterone. Although metabolic homeostasis is not maintained by intermittent GnRH-antagonist therapy alone, it is maintained by the combination of intermittent GnRH-antagonist and a progestin, which combination inhibits ovulation while assuring that proliferative endometrium will be shed during menses. This action negates the risk of endometrial carcinoma due to unopposed estrogen. The combination therapy 1) synergistically enhances the contraceptive action of each, 2) reliably inhibits ovulation, and 3) provides for cyclic menstruation.

Although this invention employs progestin as well as GnRH-antagonist administration, it will be apparent that because contraception is achieved by the GnRH-antagonist alone, if a normal menstrual cycle is not mandated, for example, where the GnRH-antagonist is to be administered only on a short term basis, e.g., when only temporary contraception is desired for medical reasons, the progestin can be omitted, in which case a normal menstrual cycle will not occur until GnRH-antagonist administration is terminated. However, because the GnRH-antagonist and the progestin collectively mimic a normal menstrual cycle, they are preferably employed together in accordance with this invention to avoid the potential adverse effects of a retained endometrium.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees celsius; unless otherwise indicated, all parts and percentages are by weight.

EXAMPLES

Materials and Methods

Fifteen adult (3.8–6.1 kg) cynomolgus monkeys (Macaca fascicularis) with regular ovulatory menstrual cycles were subjected to protocols of GnRH-antagonist treatment. The methods of feeding, housing, blood collection, and drug administration were described previously. Goodman, A. L. et al. Composite pattern of circulating LH, FSH, estradiol, and progesterone during the menstrual cycle in cynomolgus monkeys, Proc. Soc. Exp. Biol. Med 155:479.

Study I. The GnRH-antagonist employed was [Ac-4ClDPhe$^1$, 4ClDPhe$^2$, DTrp$^3$, DArg$^6$, DAla$^{10}$) GnRH. Based on previous dose studies demonstrating profound suppression of serum LH and FSH levels by this agent at a daily dose of 1 mg/kg, a higher single dose was chosen for weekly administration. Since the dominant follicle was likely to be selected by cycle day 7, the intermittent dose of GnRH-antagonist might achieve its ablation, thereby causing initiation of a new follicular phase. The GnRH-antagonist was suspended in sesame oil and injected im.

Eight monkeys were used to test ovulation inhibition. Drug administration began on day 3 after spontaneous onset of menses, when a single dose of 10 mg/kg was injected. This initial injection was followed at weekly intervals with single doses of 5 mg/kg on days 10, 17, and 24. During the first 42 days after initiation of the pretreatment menstrual flow, femoral blood (3.5 ml) was obtained on alternate days on day 43, the frequency of blood drawing was decreased to twice weekly through day 64, when the study was terminated. Throughout, sera were harvested and frozen for subsequent RIA. During the 4 weeks of GnRH-antagonist treatment, laparoscopies were performed at weekly intervals to assess ovarian status.

Study II. To clarify the mechanisms(s) by which the GnRH-antagonist blocked estrogen-induced LH surges in Study I, normal ovulatory monkeys received the GnRH-antagonist daily (2 mg/kg in sesame oil) from either days 2 through 9 or days 2 through 6 of the menstrual cycle, respectively, and estradiol (Ez) benzoate 50 ug, im; n=3) or GnRH 50 ug, iv; n=4) was given on day 6. Because the weekly treatment regimen used in study I was so inherently volatile, with GnRH-antagonist suppression of pituitary function followed by transient recovery in a series of four episodes, a daily regimen in study II was selected to achieve steadier, more consistent conditions. Estrogen challenge and GnRH challenge tests provided an evaluation of pituitary gonadotropin secretory status during the GnRH-antagonist regimen; serum LH concentrations served as the principal end point. The same test was given to three control monkeys (not given GnRH-antagonist) on day 6 of the normal menstrual cycle.

RIAs for $E_2$, progesterone ($P_4$), LH, and FSH were performed as described previously. Goodman A. L. et al., Endocrinology 1977, 100:155; Niswender G. D. et al., Endocrinol 1971, 88:1327. The monkey LH RIA had an intraassay variation of 1.9–5.0% and an interassay variation of 9.3–18.7%.

Tests for significant differences ($P<0.01$) of the intervals from the onset of menstruation to the next LH surge and/or ovulation and the menstrual interval were performed using the F statistic. Freund, J. E., "Manual of Experimental Statistics", (Prentice-Hall, Pub., Englewood Cliffs (1960).

During the 4-week course of intermittent GnRH-antagonist treatment in study I, there were no ovulation sites seen at laparoscopy. Moreover, the absence of ovulation was confirmed by the lack of serum $P_4$ elevations; also, no LH surges were found.

It was evident from means peripheral serum $E_2$ levels immediately before and on the day after the four GnRH-antagonist treatments are shown there was no sustained suppression of $E_2$ in serum; that is, $E_2$ concentrations remained near the level found in the early follicular phase of normal ovarian/menstrual cycles 90–125 pg/ml).

None of the animals with ovulation inhibition and absence of LH surges during treatment as well as resumption of an ovulatory ovarian cycle after treatments, after discontinuation of treatment with the GnRH-antagonist, serum $E_2$ levels rose within 3 weeks and were followed by timely LH surges in six of either monkeys. Presumed ovulation was indicated by typical $P_4$ elevations in serum and an ensuing luteal phase of normal length. The levels of $E_2$ and $P_4$ in the circulation were consistent with single ovulations. The means interval from the last GnRH-antagonist treatment to the subsequent preovulatory $E_2$ peaks and LH surges was approximately 14 days among the six monkeys who resumed ovulatory menstrual cycles during the study interval. The remaining two monkeys did not resume regular menstrual cycles until nearly a month after completion of this study.

Pituitary refractoriness was exhibited (three of three monkeys) to the $E_2$ benzoate challenge test given on cycle day 6 during the daily GnRH-antagonist regimen spanning days 2 through 9 (study II). There was an initial negative feedback effects of exogenous estrogen on LH and FSH secretion, the absence of familiar preovulatory-like LH surges, and finally, the resumption of apparent ovulation about 3 weeks later.

In contrast, administered GnRH (as a 50-ug bolus dose given on cycle day 6) during the daily GnRH-antagonist regimen elicited unambiguous LH responses (four of four monkeys) of seemingly normal strength and duration. All responses exceeded 4-fold elevations and did not differ significantly from the responses of control monkeys given the same iv bolus dose of GnRH.

In six of the eight monkeys, ovulation resumed promptly after the last GnRH-antagonist administration; the first post treatment estradiol peak occurred 14.3 ±3.8 (±SEM) days after the final dose.

These tests established that GnRH-antagonists achieve female contraception when given using an intermittent (weekly) treatment regimen.

Monkeys previously having regular ovarian/menstrual cycles had no ovulation (32 of 32 treatment intervals) when the GnRH-antagonist was administered once weekly. After cessation of GnRH-antagonist therapy, ovulation resumed promptly in 6 of 8 monkeys. That some monkeys regained ovulatory inhibition as soon as 8–10 days after the final dose of GnRH-antagonist suggests that a weekly treatment interval may be near the upper limit for maintenance of ovulation inhibition at the dose tested here. These observations correlate well with earlier experience in monkeys (Goodman AL & Hodgen GD, Endocrinology 19779 104:1304; diZerega GS et al., J. Clin Endocrinol Metab 1980, 50:1046) and women (Nilsson L. et al., Fertil Steril 1982, 37:30) undergoing surgical ablation of the putative dominant follicle, in whom destruction of the largest visible follicle delayed ovulation by causing reinitiation of a new follicular phase. It is possible that each weekly dose of GnRH-antagonist caused artesia of the newly selected dominant follicle. The intermittent elevations of $E_2$ in serum may reflect its secretion by newly recruited follicles in the next growing cohort. Goodman & Hodgen, supra.

Although two monkeys given the GnRH-antagonist had longer delays before resuming regular menstrual cycles, their suppressed status ended less than 60 days after the cessation of treatment.

In regard to the mechanism(s) by which the intermittent (weekly) GnRH-antagonist regimen prevented ovulation, the data from study II indicate that the estrogen-positive feedback for the LH surge was negated. During the normal follicular phase, $E_2$ benzoate will induce midcycle-like LH surges within 48 h; the GnRH-antagonist clearly negated this estrogen-positive feedback. Williams RF et al. J. Clin. Endocrinol Metab 49:422; Hodgen GD Fertil Steril 1982 38:281. In contrast, the response to GnRH was normal. It is possible that the iv bolus dose of GnRH displaced the GnRH-antagonist from gonadotroph receptors, so that the exogenous GnRH elicited normal LH secretory responses. An alternative interpretation is that the dose of GnRH-antagonist was submaximal, since previously a "medical hypophysectomy"-like status was achieved with only 50% of the dose used in these experiments. Kenigsberg et al., supra (1984).

STUDY III. In this study, which is reported in more detail in Contraception, June, 1990, Vol. 31. No. 6, pp. 623-631, six regularly cycling adult female cynomolgus monkeys (*Macaca fascicularis*) were housed in individual cages in a controlled environment and checked daily for menstrual flow. Each primate underwent a study entry control menstrual cycle in which alternate day blood samples were taken (under ketamine anesthesia, 10 mg/kg, im) to verify maturation of the dominant follicle, presumed ovulation, and corpus luteum function. The experimental design is depicted in FIG. 1. On menstrual cycle days 2, 9, 16, and 23 (onset of menses = Day 1) three of the monkeys were injected sc with 0.1 mg/kg GnRH-antagonist ([Ac-$D_2Nal^1$, $4ClDPhe^2$, $D_3Pal^3$, $Arg^5$,$DGlu^6$ (AA), $DAla^{10}$]- GnRH; Nal-Glu) in saline. This dose was selected based on dose-response findings reported in Fertil Seril 1987; 48:480-485. On cycle days 15 to 26, each female was administered 25 μg norgestimate/day orally. This treatment regimen (once-weekly GnRH-antagonist plus 12 days of progestin) was repeated for 2 additional cycles (84 days total). Two of the treated monkeys were ovariectomized at the end of the third treatment cycle to evaluate ovarian follicular morphology. The remaining female was allowed to demonstrate recovery of ovulatory menstrual cycles prior to ovariectomy. Three control monkeys received saline injections and blank (progestin placebo) capsules according to the same regimen. Serum samples were assayed by RIA for estradiol, progesterone, LH, and FSH.

Following a typical control cycle, weekly sc injections of Nal-Glu GnRH-antagonist effectively blocked completion of follicular maturation, ovulation, and corpus luteum function as judged by serum LH, $E_2$, and P levels. Serum progesterone was undetectable ($<0.1$ ng/ml) during the treatment cycles. Several episodic bursts of LH secretion were observed without being regarded as preovulatory LH surges; that is, these sporadic LH elevations were not temporally associated either with progressive estradiol elevations or with subsequent luteal phase-like progesterone patterns. Importantly, serum estradiol levels during GnRH-antagonist plus norgestimate treatments were maintained at 35 ±7 pg/ml. Following the cessation of daily norgestimate administration on day 26 in each treatment cycle, menses uniformly occurred within 2 or 3 days. "Spotting" or "breakthrough bleeding" between these intervals of overt menstruation were not detected. Recovery of apparently normal menstrual cycles, as judged by timely estradiol elevations, midcycle LH surges, and luteal phase progesterone patterns, were manifested without delay following termination of the final treatment cycle.

The results of this study confirm that once weekly administration of low dose Nal-Glu GnRH-antagonist effectively blocked maturation of the dominant follicle, thereby preventing ovulation and corpus luteum function. NO LH surges or serum progesterone rises were detected during the intermittent GnRH-antagonist regimen; apparently no ovulations occurred. Moreover, the sequential application of norgestimate effectively transformed proliferative to secretory endometrium. Histological sections on day 26 revealed appropriate late-secretory phase endometrial status; menses promptly and uniformly followed withdrawal of daily norgestimate administration. The absence of "breakthrough bleeding" suggests an adequate endogenous estrogen supply subsequently combined with the progestin. No evidence of follicular cyst formation was observed. Ovarian histology, both immediately following and two months after cessation of GnRH-antagonist plus norgestimate treatment, revealed multiple small and medium-sized developing and atretic follicles, indicative of sequential ablation of progressive folliculogenesis. In addition, no residual effects were detected following this treatment regimen. Apparently normal hypothalamic-pituitary-ovarian-uterine function resumed immediately following cessation of GnRH-antagonist plus norgestimate treatment.

Importantly, peripheral levels of endogenous ovarian estradiol during GnRH-antagonist plus norgestimate treatment were maintained at approximately 35 ±/ pg/ml, consistent with serial (weekly) ablation of follicular maturation. Although not measured here, the biological effects of estrone would add to those of estradiol. As shown earlier in a similar primate model, the total estrogen level in peripheral circulation is substantial often fluctuating between 50 and 100 pg/ml. Kenigsberg, D. and Hodgen, G. B., Recent Progress in Hormone Research (New York:Academic Press, 1983:39:1–73).

Although the optimal dose and regimen of the GnRH-antagonist has not yet been established experimentally, the data obtained to date demonstrate the feasibility of a new ovulation inhibition method using a once weekly dose of GnRH-antagonist plus a progestin to control endometrial growth. The advantages of a contraceptive method which relies on natural estrogens (instead of synthetic analogs) and a maximum of only about 12 days of progestin exposure each month (instead of 21 days) are readily apparent. However, more exclusive studies will probably confirm that the daily progestin dose selected for this study can be reduced because it is the GnRH-antagonist which prevents ovulation, as opposed to conventional oral contraceptive formulations, wherein the progestins dominate to provide assurance that ovulation will be blocked.

Kit Exam

A kit is prepared which contains four unit doses adapted for self-administration of the GnRH-antagonist [Ac-D4ClPhe$^1$,D4ClPhe$^2$,DTrp$^3$,D-Arg$^6$.DAla$^{10}$)GnRH: 11 conventional tablets adapted for oral ingestion, each containing 0.1-0.5 mg. of the progestin norgestrel; a 4-week chart on which the first day of menses can be oriented with the day of the week on which it occurs as day 1 of the 4 week chart and administration instructions. Days 2, 9, 16, and 23 on the chart (which are aligned with the same day of the week) bear indica informing the female to self-administer, in the manner and by the route indicated in the instructions, a unit dosage of the GnRH-antagonist on those days. Days 15 through 25, inclusive, bear indica informing the female to ingest one of the progestin tablets on each of those days. The instructions inform the female to obtain a second kit for the next menstrual cycle.

A gonadal female who self-administers the GnRH-antagonist and progestin according to the above-described schedule achieves contraception while maintaining an otherwise normal menstrual cycle of about 30 days.

a) In one form, the GnRH-antagonist is in admixture with a dry diluent, e.g., dextrose, in the form of a dry micronized powder which is dispensed from a conventional pressurized (under $CO_2$) container which is springload mounted in a conventional inhalator which dispenses about 10 mg of the GnRH-antagonist when the container is depressed into the inhalator. The instructions accompanying the inhalator instruct the female to activate the inhalator twice while inhaling, on the same day of each week as indicated by the chart.

b) In another form otherwise corresponding to a), the inhalator dispenses about 75 mg of the GnRH-antagonist each time the container is squeezed.

c) In another form otherwise corresponding to a), the GnRH-antagonist is present in four conventional foil wrapped anhydrous suppositories, each containing 150 mg. thereof, and the instructions instruct the female to insert one of the suppositories into the rectum on each day of the week indicated on the chart.

d) In another form otherwise corresponding to a), the GnRH-antagonist is present in four conventional dry, foil wrapped saliva dissolvable lozenges, each containing 150 mg thereof, and the instructions instruct the female to dissolve a lozenge under the tongue on the same day of each week as indicated by the chart.

e) In variations of each of the kits described hereinabove, the norgestrel in the tablets is replaced by 1 mg of norethindrone, 5 mg of norethynodrel, 1 mg of ethynodiol diacetate or 0.2 mg of levonorgestrel.

f) In other variations of each of the kits described hereinabove, the GnRH-antagonist therein is replaced by a GnRH-antagonist of U.S. Pat. Nos. 4,409,208; 4,444,759; 4,547,370; 4,565,804; 4,569,927; or 4,619,914.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of providing contraception and regulating of a menstrual cycle of a gonadal female mammal, without blocking hormonogenesis, which comprises the steps of (a) administering to the female on day 1, 2 or 3 of her menses and thereafter at about once every 7 days an amount of a GnRH-antagonist effective to block folliculogenesis thereby creating a contraceptive state during that cycle, but less than the amount thereof required to block hormogenesis; and (b) inducing menses by administering to the female only during the last two weeks of that cycle an amount of a progestin effective to produce a secretory endometrium and then terminating the progestin administration.

2. The method of claim 1, wherein the female mammal is a human and the steps are repeated on successive menstrual cycles.

3. The method of claim 2, wherein the GnRH-antagonist is administered initially on day 1 or 2 of menses.

4. The method of claim 2, wherein the GnRH-antagonist is administered topically.

5. The method of claim 2, wherein the GnRH-antagonist is [Ac-D4ClPhe$^1$, D4ClPhe$^2$,DTrp$^3$,DArg$^6$,DAla$^{10}$)GnRH.

6. The method of claim 2, wherein the progestin is orally active and is administered orally.

7. The method of claim 1, wherein the progestin is administered daily during at least the last two weeks of the menstrual cycle for at least ten days.

8. The method of claim 2, wherein the progestin is administered daily from about day 15 to about day 26 of the menstrual cycle.

9. The method of claim 2, wherein the progestin is norethindrone, norethynodrel, ethynodiol diacetate, norgestrel or levo-norgestrel.

10. The method of claim 2, wherein the GnRH-antagonist is administered once every 7 days of the menstrual cycle, initially on day 1 or 2 of menses.

11. The method of claim 10 wherein the GnRH antagonist is [Ac-D4ClPhe$^1$, D4ClPhe$^2$,DTrp$^3$,DArg$^6$,DAla$^{10}$)GnRH.

12. The method of claim 10 wherein the progestin is norethindrone, norethynodrel, ethynodiol diacetate, norgestrel or levo-norgestrel.

13. The method of claim 12, wherein the GnRH-antagonist is [Ac-D4ClPhe$^1$D4ClPhe$^2$,DTrp$^3$,DArg$^6$,DAla$^{10}$)GnRH.

14. The method of claim 1, wherein the female mammal is a human and the steps are repeated on successive menstrual cycles; wherein the GnRH-antagonist is administered initially on day 1 or 2 of menses and thereafter once every 7 days; wherein the progestin is orally active and is administered orally daily during at least the last two weeks of the menstrual cycle for at least ten days.

15. The method of claim 14, wherein the GnRH-antagonist is [Ac-D4ClPhe$^1$, D4ClPhe$^2$, KTrp$^3$, DArg$^6$, DAla$^{10}$]GnRH.

* * * * *